United States Patent
Hufnagel

(10) Patent No.: US 10,271,996 B2
(45) Date of Patent: Apr. 30, 2019

(54) DEVICE FOR AN EVERSION ASSIST OF INVERTED NIPPLES

(71) Applicant: Zorka Hufnagel, Palm Harbor, FL (US)

(72) Inventor: Zorka Hufnagel, Palm Harbor, FL (US)

(*) Notice: Subject to any disclaimer, the term of this patent is extended or adjusted under 35 U.S.C. 154(b) by 141 days.

(21) Appl. No.: 15/266,868

(22) Filed: Sep. 15, 2016

(65) Prior Publication Data

US 2018/0000652 A1   Jan. 4, 2018

Related U.S. Application Data

(60) Provisional application No. 62/356,357, filed on Jun. 29, 2016.

(51) Int. Cl.
*A61F 13/14* (2006.01)

(52) U.S. Cl.
CPC .................................. *A61F 13/145* (2013.01)

(58) Field of Classification Search
CPC ..... A61F 13/145; A61F 13/25; A61F 13/0259
See application file for complete search history.

(56) References Cited

U.S. PATENT DOCUMENTS

| | | | | |
|---|---|---|---|---|
| 4,754,750 A * | 7/1988 | Imonti | ............... | A61F 15/008 128/888 |
| 5,171,321 A * | 12/1992 | Davis | ............... | A61F 2/52 128/890 |
| 5,267,970 A * | 12/1993 | Chin | ............... | A61M 25/02 604/174 |
| 5,445,142 A * | 8/1995 | Hassler, Jr. | ............... | A61B 1/00087 600/105 |
| 5,743,272 A * | 4/1998 | Kocher, Jr. | ............... | A61J 13/00 128/846 |
| 5,847,404 A * | 12/1998 | Grady | ............... | A61F 13/12 250/515.1 |
| 7,487,779 B2 * | 2/2009 | Kurz | ............... | A61F 15/008 128/889 |
| 8,808,262 B2 * | 8/2014 | Krasikoff | ............... | A61F 13/14 604/385.07 |
| 2011/0247636 A1* | 10/2011 | Pollack | ............... | A61F 15/008 128/890 |
| 2014/0200529 A1* | 7/2014 | Hyde-Edwards | ............... | A61F 13/145 604/304 |
| 2015/0175115 A1* | 6/2015 | Sandt | ............... | B60R 21/201 280/743.1 |
| 2017/0027760 A1* | 2/2017 | Ji | ............... | A61F 13/022 |

* cited by examiner

*Primary Examiner* — Kristen Matter
(74) *Attorney, Agent, or Firm* — Paul Murty; Smith & Hopen, P.A.

(57) ABSTRACT

The invention is a single-unit areolar device of ultralight construction with an adhesive back that relies on no additional parts or components to effectively manipulate nipple orientation for eversion assist. The device builds upon the interplay between the adhesive-back flat base with the areola tissue to create a gentle, focused nudge to evert assist and maintain protraction of inverted nipples. The ultralight single-unit device is comfortable to wear for extended periods of time, easily concealed beneath clothing, and remains securely in place while active or asleep. The disposable attributes of the cost effective materials utilized lend further advantage to the device.

20 Claims, 3 Drawing Sheets

DEVICE FOR AN EVERSION ASSIST OF INVERTED NIPPLES

PRIORITY CLAIM

This application claims priority to U.S. Provisional Application Ser. No. 62/356,357, filed Jun. 29, 2016. The above referenced application is incorporated herein by reference as if restated in full.

BACKGROUND

Approximately 10-20 percent of the United States population suffers from inverted nipples. The condition can adversely affect self-esteem, sexuality, and, in severe cases, the ability to breastfeed. Inverted nipples, which retract into the breast, can occur in both men and women. An inverted nipple is characterized in the medical industry as Grades 1, 2, and 3. Less severe Grade 1 and Grade 2 inverted nipples may be protracted through various methods of pressure to the areola to evert the nipple, however, most return to the inverted state. The treatment method depends on the grade of the inversion, the cause of the inversion, and whether breastfeeding is planned. There are several ways to reverse the condition, ranging from manual manipulation to plastic surgery.

As of this writing, many of the solutions which appear in prior art generally involve suction, vacuum, a pump, piercing, a syringe, or multiple parts, some of which rely on a combination thereof. Problems known to be associated with the aforementioned devices and methods include skin irritation, ulceration, discomfort, unreliable attachment, poor concealability, multiple procedures, and sterilization or other maintenance. While the prior art may have fulfilled their respective particular objectives and requirements, they have not addressed the needs of today's consumer in search of an effective "user-friendly" alternative for the treatment of inverted nipples. Therefore, it is an important object of the present invention to provide a solution which minimizes the discomfort, adverse effects, number of parts, number of procedures, and amount of physical manipulation to the breast or nipple associated with prior art.

To this end, the present invention provides a single-unit apparatus of ultralight construction primarily developed for the purpose of everting inverted nipples and maintaining the protracted state with a more "user-friendly" solution which is easy to apply, unrestrictive, more comfortable to wear, more concealable beneath clothing, and better capable of remaining securely in place when active or asleep. Further adding to its "user-friendly" attributes, the present invention is constructed of ultralight and cost-effective materials to allow for disposable use.

As such, the device of the present invention for an eversion assist of inverted nipples and maintaining the protracted state substantially departs from the conventional concepts and designs of the prior art. Therefore, it can be appreciated that there exists a continuing need for a new and improved device for eversion assist and maintaining the nipples in the everted orientation. In this regard, the present invention substantially fulfills this need.

SUMMARY

In view of the disadvantages inherent in the known types of nipple everting devices now present in the prior art, the general purpose of the present invention is to provide a new and improved device and method for an eversion assist of inverted nipples which overcomes the many disadvantages associated with the prior art. The present invention is a "user-friendly" solution comprised of a generally annular single-unit device with adhesive back, which relies on the interplay between the adhesive, the areola tissue and the flat base of the device to create a gentle, yet focused nudge for effectively manipulating nipple orientation and maintaining a protracted state. As such, the present invention substantially departs from the conventional use of vacuum, suction, pumps, syringes, strong manipulation of the breast or nipple, encapsulation, or multiple parts to treat inverted nipples.

In this respect, the ultralight apparatus of the present invention offers a solution with many advantages afforded by its unique design and approach to eversion assist, including a more comfortable and securely attached device with improved concealability, which is particularly advantageous when only one nipple is inverted and requires treatment.

Adding to the aforementioned "user-friendly" attributes, the present invention provides for a new and improved eversion assist device fabricated of ultralight and cost-effective materials which lend themselves well to being configured and manufactured as a disposable utility, thus eliminating the need for sterilization or other maintenance known to prior art.

There has thus been outlined, rather broadly, the features of the invention in order that the present contribution to the art may be better appreciated. These, together with other objects of the invention, are pointed out in the accompanying drawings and descriptive matter hereinafter. There are, of course, additional features of the invention that will be described and which will form the subject matter of the claims attached. Further, the device is capable of other embodiments and being carried out in various ways, so it is to be understood that the phraseology and terminology employed herein are for the purpose of descriptions and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
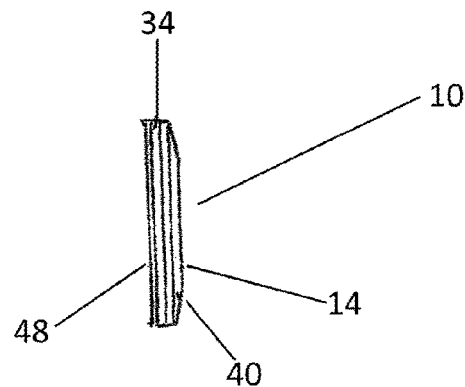
FIG. 1 is a side elevational view of a device for an eversion assist of inverted nipples, the device constructed in accordance with the principles of the present invention, the device being in use.
Figure 2:
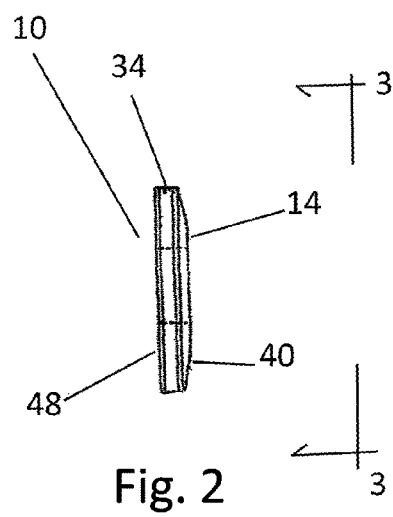
FIG. 2 is an exploded side elevational view of the device shown in FIG. 1.
Figure 4:
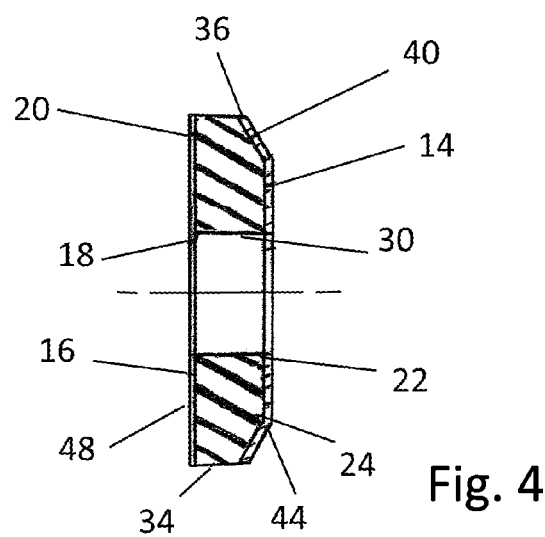
FIG. 4 is a cross sectional view taken along line 4-4 of FIG. 3.
Figure 5:
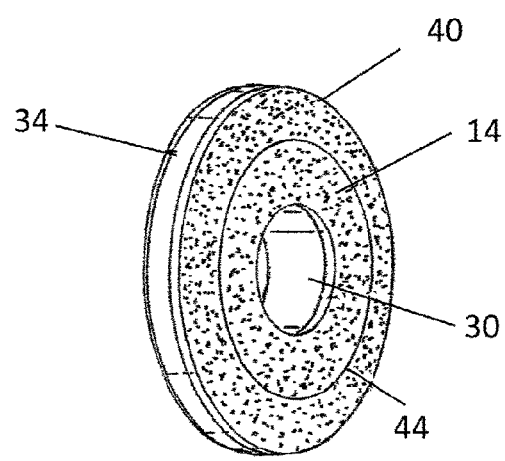
FIG. 5 is a front perspective illustration of the device shown in the prior Figures.
Figure 6:
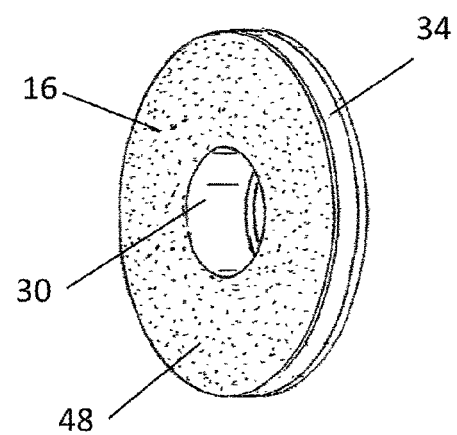
FIG. 6 is a rear perspective illustration of the device shown in the prior Figures.

With reference now to the drawings, and in particular to FIGS. 1 and 4 thereof, the preferred embodiment of the new and improved device for an eversion assist of inverted nipples embodying the principles and concepts of the present invention and generally designated by the reference numeral 10 will be described.

The present invention, the device for an eversion assist of inverted nipples 10, is comprised of a plurality of components. Such components in their broadest context include upper and lower surfaces, a central aperture, and an exterior periphery. Such components are individually configured and correlated with respect to each other so as to attain the desired objective.

More specifically, the present invention is a uniquely "user friendly" apparatus of ultralight materials comprising a multi-layered single-unit construction with adhesive back. The device of the present invention includes a substantially annular raised composite with aperture which fits over the areola and relies upon the interplay between the device's flat base, the adhesive and the areola tissue to manipulate the nipple orientation and maintain a protracted state. Unlike products comprising the prior art, many of which utilize suction, vacuum and are often cumbersome methods/devices, the present "user friendly" invention effectively treats inverted nipples by means of a continuous gentle, yet focused nudge effect achieved when the adhesive-back flat base of the device meets with the areola tissue.

Further benefits of this new and improved solution for treating inverted nipples relate to the device's ultralight construction and adhering properties, which make this device easy to apply, comfortable to wear for extended periods, capable of remaining securely in place while active or asleep, as well as affording improved concealability over prior art, which can be particularly advantageous when only one nipple is inverted. Adding to its "user-friendly" attributes, this self-adhering ultralight device can be configured to be efficiently manufactured for disposable use, including peel-and-stick properties, thus eliminating the need for maintenance.

The present invention comprises a 3-dimensional, substantially annular, multi-tiered composite areolar device measuring from 0.25"-1", (6.35 mm-25.4 mm) thickness. The topcoat is comprised of a thin membrane of latex, felt, moleskin, silicone or other lightweight polymer. The topcoat is bonded to an inner layer of ultralight material to provide firmness and cushioning. This ultralight material substance is firm enough to allow the device to be firmly pressed against the surface of the areola. The flat bottom layer is a self-sticking medical grade adhesive that is bonded to the bottom external layer of the device.

This self-sticking adhesive is characterized as having: a tackiness of 10-450 grams as determined by a ChemInstruments polyken probe tack tester and a tensile strength of 0.14-5.52 mega Pascals (20-800 pounds/square inch), a minimum elongation of 250-1100 percent and a tear strength of 0.88-35.2 kN/m, 5-200 pounds/square inch.

The overall diameter of the device measures between 1"-4", (25.4 mm-101.1 mm) diameter with a center aperture between 0.25"-1", (6.35 mm-25.4 mm) that are manufactured into rings to conform to various areola and nipple sizes.

Specifically, the device is designed to address the condition presented by Grade 1 and Grade 2 inverted nipples, i.e. those protractible with light inward pressure to the areola.

This "user-friendly" single-unit device can be applied with little time or effort involved. First, by using a method that is most comfortable to the user, the nipple is protracted. If the nipple cannot be everted easily, a doctor should be consulted. Second, remove the protective backing to expose the adhesive and apply the device so the nipple protrudes through the center opening, then gently press onto the areola. The affected result is that the device applies a slight pressure inward and upward to the areola tissue around the nipple base creating a continuous gentle, yet focused nudge-effect, while also keeping the areola tissue from spreading and thereby allowing for possible tightening around the nipple base which may prove beneficial for lasting results. Once applied, the device may be worn comfortably and securely, with or without clothing, for extended periods of time.

With continued use, results can vary, to include long lasting protraction in some users. Because of the small size and ultralight design of this device, one can expect the least amount of discomfort or intrusion upon the natural freedom of the breast and nipple.

Several attributes include its easy of application and use. The device may be worn comfortable for extended periods of time. The device is light weight and nearly invisible under clothing. The device need not rely on suction, creams, multiple parts, or piercing, but instead may rely on an ultra-light adhesive backing. The device does not require obtrusive hardware. Nor does the device require on-going cleaning or sterilization.

The present invention is a device 10 for an eversion assist of inverted nipples. The device is fabricated of ultralight material and has a generally three-dimensional annular configuration with an upper layer or upper planar surface 14 and a parallel lower planar surface 16.

A cylindrical aperture 28 extends centrally through the device. The central aperture has an interior periphery or interior surface of the aperature 30 in a cylindrical configuration extending between the lower planar surface and the upper planar surface. The cylindrical aperture has a second central axis co-extensive with the first central axis. The cylindrical aperture generally has a diameter of 25 percent (25%) of the lower diameter.

The lower planar surface 16 has a radially interior edge or aperture opening 18 and a radially exterior edge 20. The upper planar surface 14 has a radially interior edge 22 and a radially exterior edge 24. The device has a first central axis. The lower peripheral surface has a lower diameter of from 1 to 4 inches. The upper planar surface has a diameter of from 70 to 100 percent (70%-100%) of the lower diameter. The device generally has a height of from 12.5 to 25 percent (12.5%-25%) of the lower diameter.

The device has a lower exterior periphery 36 in a cylindrical configuration extending upwardly from the radial exterior edge of the lower planar surface and terminating at an intermediate circle 44. The lower exterior periphery has a peripheral height of from 65 to 100 percent (65%-100%) of the height of the device.

The device may have an upper exterior periphery 40 in a frusto-conical configuration extending upwardly from the intermediate circle and terminating at the radially exterior edge of the upper planar surface.

An upper layer 14 of a cover material is adhered to the upper surface and the upper exterior periphery. The upper layer is comprised of a thin membrane chosen from the class comprised of latex, elastomer, felt, moleskin, silicone, or other lightweight polymer.

A lower layer 48 is a self-sticking tacky adhesive or adhesive layer adhered to the lower surface. The lower layer is comprised of a medical grade adhesive.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The device can be described as a combination of other features as well. The device 10 may be a single-unit mold or a composite of multiple plies adhered together. The device may be made of a latex layer or be entirely latex-free. The device may be made of a synthetic or natural polymer. The device may be made of Poron. The diameter of the device may be from 1.5 to 4 inches. The thickness of the device may be from 0.125-1 inches.

Figure 3:
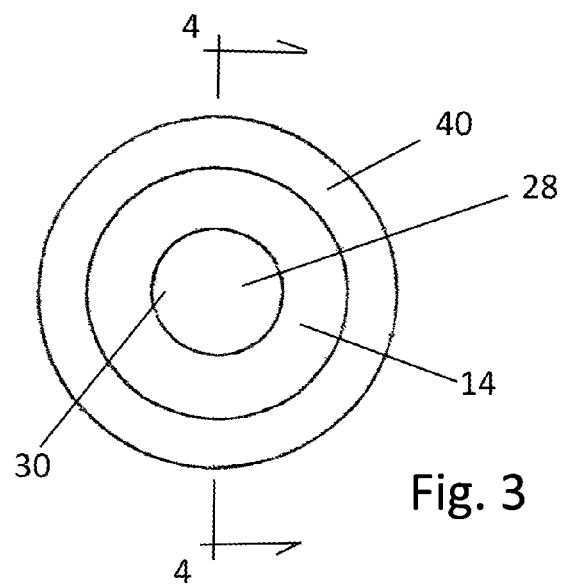
FIG. 3 is a front elevational view taken along line 3-3 of FIG. 2.

The device may comprise an upper layer 14, an adhesive layer 48, and an aperture 28, as shown in FIGS. 3 and 4. The device may also feature a substantially flat portion which may be conterminous with the lower planar surface 16. The exterior, which may be conterminous with lower exterior periphery 36, the upper exterior periphery 40, and the upper layer 14, may have a straight, tapered, spherical, conical, frustoconical, angular edge, polygonal, or ovoid shape.

The upper layer may feature a substantially flat upper surface and a flat lower surface, which may be the same as the lower planar surface 16, and may be made of felt, moleskin, foam, latex, elastomer, silicone, another flexible polymer, or a combination of these materials. The upper layer may serve as an exterior of the device. The lower surface of the upper layer may be disposed flush against the adhesive layer.

The adhesive layer may be configured to adhere to an areola tissue to manipulate nipple orientation. Specifically, it may be configured to adhere at least a portion of the areola tissue into a position parallel to the substantially flat portion. It may be formed from woven fabric, and/or feature a plastic portion or latex portion. The adhesive layer may be protected by a protective back material (not shown). This protective back material may be removably attached to the adhesive layer. The protective back material may feature a tag enabling easy removal.

The aperture may be disposed centrally in the device. It may be contoured to receive a nipple when at least a portion of the areola tissue is oriented in a position parallel to the substantially flat portion. The configuration of the aperture may be such that the nipple may enter though a gap in the adhesive layer. The aperture may be cylindrical, conical, frustoconical, or spherical in shape. The inner surface of the aperture 30 may feature a continuation of the adhesive layer or the adhesive layer may terminate at or near the opening of the aperture 18. The diameter of the aperture may range from 0.25 to 1 inch.

The invention claimed is:

1. An annular, single-unit device for the treatment of inverted nipples without requiring suction or encapsulation comprising:

a device base, an aperture, and an adhesive layer;

the device base being firm and having an upper surface and a bottom surface, the bottom surface being substantially flat;

the aperture being substantially cylindrical, extending centrally through the device, and comprising a first opening, a second opening, and an inner surface, the first opening being disposed on the upper surface of the device base, the second opening being disposed on the bottom surface of the device base;

the adhesive layer being disposed on the bottom surface of the device base;

the adhesive layer being configured to adhere to an areola tissue, the device base in conjunction with the adhesive layer configured to flatten and manipulate the areola tissue into an orientation parallel to the device base;

the second opening of the central aperture being configured to receive a nipple, the first opening of the central aperture configured to further receive the nipple and permit the nipple to pass through the first opening;

the inner surface of the central aperture being configured to receive the nipple through a gap in the adhesive layer;

the device having an overall thickness at least 0.125" and thin enough for the nipple to protrude through the first opening;

the device base being firm enough and an adhesive of the adhesive layer strong enough to pull at a perimeter of the areola tissue and push an area around the nipple base to emulate a manual nudge for manipulating nipple orientation to the everted state.

2. The device of claim 1, wherein the device base is further firm enough and the adhesive of the adhesive layer is further strong enough to exert a continuous inward pressure to the areola tissue surrounding the nipple base to manipulate nipple orientation to the everted state and maintain nipple protraction.

3. The device of claim 1, the device base being made of foam.

4. The device of claim 1, the device base being made of PORON®.

5. The device of claim 1, wherein the device base is further firm enough and the adhesive of the adhesive layer is further strong enough to prevent the areola tissue from spreading and promote tightening around the nipple base when worn continuously for extended periods to effectuate lasting protraction.

6. The device of claim 1, further comprising a protective backing material removably attached to the adhesive layer and configured to be removed before the adhesive layer adheres to the areola tissue.

7. The device of claim 1, an exterior portion of the device being spherical.

8. The device of claim 1, an exterior portion of the device having a tapered, conical, or frusto-conical shape.

9. The device of claim 1, the device base having a diameter of 1.5 to 4 inches.

10. The device of claim 1, the adhesive layer having a tackiness of 10-450 grams, a tensile strength of 0.14-5.52 mega Pascals, a minimum elongation of 250-1100 percent and a strength of 0.88-35.2 kN/m.

11. The device of claim 1, the device at least partially made of a flexible polymer.

12. An annular, disposable, single-unit device for the treatment of inverted nipples without requiring suction or encapsulation comprising:

a device base, an aperture, and an adhesive layer;

the device base having an upper surface and a substantially flat bottom surface;

the aperture being substantially cylindrical, having a diameter of 0.25-1", extending centrally through the device, and comprising a first opening, a second opening, and an inner surface, the first opening being disposed on the upper surface of the device base, the second opening being disposed on the bottom surface of the device base;

the adhesive layer being disposed on the bottom surface of the device base and configured to adhere to an areola tissue;

the second opening of the central aperture being configured to receive a nipple, the first opening of the central aperture configured to further receive the nipple and permit the nipple to pass through the first opening;

the inner surface of the central aperture being configured to receive the nipple through a gap in the adhesive layer;

the device base in conjunction with the adhesive layer configured to flatten and manipulate the areola tissue into an orientation parallel to the device base;

the device base being firm enough and an adhesive of the adhesive layer strong enough to pull at a perimeter of the areola tissue and push an area around the base of the nipple to manipulate nipple orientation to an everted state, and to exert a continuous inward pressure to the areola tissue surrounding the nipple base to manipulate nipple orientation to the everted state and maintain nipple protraction;

the device being at least 0.125" thick but thin enough for the nipple to protrude through the first opening.

13. The device of claim 12, the device not being made of rubber or latex.

14. The device of claim 12, the adhesive layer comprising a medical grade adhesive.

15. The device in claim 12, the device base formed as a single mold composite formed of a plurality of plies.

16. The device of claim 12, the adhesive layer having a tackiness of 10-450 grams, a tensile strength of 0.14-5.52 mega Pascals, a minimum elongation of 250-1100 percent and a strength of 0.88-35.2 kN/m.

17. A method of correcting inverted nipples without requiring suction or encapsulation comprising the steps of:
providing an annular, disposable, single-unit device comprising:
a device base, an aperture, and an adhesive layer;
the device base being firm and having an upper surface and a substantially flat bottom surface;
the aperture being substantially cylindrical, extending centrally through the device, and comprising a first opening, a second opening, and an inner surface, the first opening being disposed on the upper surface of the device base, the second opening being disposed on the bottom surface of the device base;

the adhesive layer being disposed on the bottom surface of the device base and comprising a protective backing;

the adhesive layer being configured to adhere to an areola tissue, the device base in conjunction with the adhesive layer configured to flatten and manipulate the areola tissue into an orientation parallel to the device base;

the second opening of the central aperture being configured to receive a nipple, the first opening of the central aperture configured to further receive the nipple and permit the nipple to pass through the first opening;

the inner surface of the central aperture being configured to receive the nipple through a gap in the adhesive layer;

the device being at least 0.125" thick, but thin enough for the nipple to protrude through the first opening;

the device base being firm enough and an adhesive of the adhesive layer strong enough to pull at a perimeter of the areola tissue and push an area around the nipple base to emulate a manual nudge for manipulating nipple orientation to an everted state;

protracting the nipple manually to a furthest extent possible;

removing the protective backing from the adhesive layer;

centering the device with the aperture over the nipple;

pressing the device onto the areola tissue so the nipple passes fully through the second opening of the aperture and protrudes through the first opening of the aperture;

maintaining the device on the areola tissue continuously for at least twenty-four hours and even while a wearer of the device is sleeping;

removing and disposing of the device;

applying additional eversion assist devices by repeating application steps until the nipple remains naturally protracted.

18. The method of claim 17, the adhesive layer having a tackiness of 10-450 grams, a tensile strength of 0.14-5.52 mega Pascals, a minimum elongation of 250-1100 percent and a strength of 0.88-35.2 kN/m.

19. The method of claim 17, wherein the device is further firm enough and the adhesive of the adhesive layer is further strong enough to prevent the areola tissue from spreading and promote tightening around the nipple base when worn continuously for extending period to effectuate lasting protraction after the device is removed.

20. The method of claim 17, the device having an overall combined layer thickness of less than 1 inch.

* * * * *